(12) United States Patent
Jaynes

(10) Patent No.: US 9,163,066 B2
(45) Date of Patent: Oct. 20, 2015

(54) ANTIMICROBIAL LYTIC PEPTIDES

(75) Inventor: Jesse Michael Jaynes, Auburn, AL (US)

(73) Assignee: AGROMED LLC, Anapolis, MD (US)

( * ) Notice: Subject to any disclaimer, the term of this patent is extended or adjusted under 35 U.S.C. 154(b) by 171 days.

(21) Appl. No.: 13/134,828

(22) Filed: Jun. 17, 2011

(65) Prior Publication Data

US 2014/0128312 A1    May 8, 2014

Related U.S. Application Data

(60) Provisional application No. 61/398,640, filed on Jun. 29, 2010.

(51) Int. Cl.
| | |
|---|---|
| *C07K 14/00* | (2006.01) |
| *C07K 7/08* | (2006.01) |
| *C07K 14/47* | (2006.01) |
| *A61K 38/03* | (2006.01) |
| *A61K 38/17* | (2006.01) |

(52) U.S. Cl.
CPC . *C07K 14/00* (2013.01); *C07K 7/08* (2013.01); *C07K 14/4723* (2013.01); *A61K 38/03* (2013.01); *A61K 38/1729* (2013.01)

(58) Field of Classification Search
CPC ....... A61K 38/02; A61K 38/10; A61K 38/16; A61K 38/03; A61K 38/1729; C07K 14/00; C07K 7/08; C07K 14/4723
USPC .................. 514/2.4; 530/324, 326
See application file for complete search history.

(56) References Cited

U.S. PATENT DOCUMENTS

| | | | | |
|---|---|---|---|---|
| 6,084,156 A | * | 7/2000 | Garbabino et al. | 800/301 |
| 2008/0153748 A1 | * | 6/2008 | Jaynes | 514/12 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*

* cited by examiner

*Primary Examiner* — James H Alstrum Acevedo
*Assistant Examiner* — Erinne Dabkowski
(74) *Attorney, Agent, or Firm* — John Dodds

(57) ABSTRACT

This invention relates to novel lytic peptides which are effective in treating citrus plant diseases including canker and greening. The invention also relates to antimicrobial compositions comprising lytic peptides and the use of such compositions in methods for treating diseases of citrus plants.

4 Claims, 2 Drawing Sheets

Figure 1

Class 1

Melittin
GIGAVLKVLTTGLPALISWIKRKRQQ

DPE
FALALKALKKALKKLKKALKKAL

Class 2

Cecropin B
KWKVFKKIEKMGRNIRNGIVKAGPAIAVLGEAKAL

D2A21
FAKKFAKKFKKFAKKFAKFAFAF

Class 3

Magainin
GIGKFLHSAKKFGKAFVGEIMNS

D3E
FVKKVAKKAKKVAKKAVKVAKKV

ANTIMICROBIAL LYTIC PEPTIDES

This application claims priority under 35 U.S.C 119 (e) of U.S. Provisional 61/398, 640, filed Jun. 29, 2010. The entire contents of the prior application U.S. Provisional 61/398, 640 is incorporated herein by reference.

FIELD OF THE INVENTION

This invention relates to novel lytic peptides which are effective in treating citrus plant diseases including canker and greening. The invention also relates to antimicrobial compositions comprising lytic peptides and the use of such compositions in methods for treating diseases of citrus plants.

BACKGROUND OF THE INVENTION

Citrus fruit is produced all over the world. It is the highest value fruit crop in international trade. Essentially, there are two citrus markets: fresh and juice. Generally citrus types include oranges, grapefruit, limes, lemons and tangerines. Many countries experience serious citrus disease problems, especially those caused by canker and greening. There have been no satisfactory treatments for these citrus plant diseases as reported in Brlansky, R. H., K. R. Chung, M. E. Rogers. 2005. 2006 Florida citrus pest management guide: Huanglongbing (citrus greening) and UF/IFAS Extension.CAB International. 2000. Crop protection compendium. Wallingford, UK: CAB International.

These diseases are an immediate threat to the future of the citrus industry in Florida. The greening disease is of more recent origin in Florida, having arrived there in September of 2005. Canker has been around much longer. Canker is basically airborne spread, mainly through wind, and especially those of hurricane velocity. Greening, on the other hand, is spread through a small insect known as the Asian citrus psyllid. Both canker and greening are bacterial pathogens.

Plants do not possess a complex immunoglobulin-based system such as that found in higher vertebrates to defend themselves against attacking microbial pathogens; however, they do have a wide variety of innate host defense mechanisms at their disposal. These include the production of antimicrobial reactive oxygen species (ROS), secondary metabolites, hydrolytic enzymes, and a wide array of antimicrobial proteins and peptides. Recombinant DNA technologies and plant transformation procedures have been used to introduce and express genes encoding these types of antimicrobial agents in plants in an effort to increase host resistance to plant pathogens. Of particular interest has been the identification and characterization of ribosomally synthesized antimicrobial peptides (AMPs). The introduction of antimicrobial peptide genes into plants with demonstrated enhanced pathogen resistance by expression of their encoded peptides has been reported in Destefano-beltran L, Jaynes J M, Clark C. 1987. Effect of novel lytic peptides on plant pathogenic bacteria. Phytopathology 77, 1768 and Jaynes J M, Xanthopoulos D. Destefano-beltran L, Dodds J H 1987 Increasing bacterial disease resistance in plants utilizing anti bacterial genes from insects, Bioessays, 6, 263-70. As an example, D4E1 (AgroMed) has been tested extensively by a number of labs throughout the world and has been found efficacious in limiting pathogens of cotton, poplar and pome fruits such as pears and apples.

SUMMARY OF THE INVENTION

In light of the high cost of citrus fruit losses due to microorganism borne disease and the need to find safe and effective methods of citrus plant treatment, it is desirable to provide antimicrobial agents and compositions which offer important improvements and advantages over previous treatments.

Additional features and advantages of the present invention will be set forth in part and in a description which follows, and in part will be apparent from the description, or may be learned by practice of the present invention. The objectives and advantages of the invention will be realized and attained by means of the elements, combinations, composition, and process particularly pointed out in the written description and appended claims.

To achieve the objects and in accordance with the purpose of the present invention, as embodied and broadly described herein, the present invention relates to new and novel synthetic lytic peptides which effectively destroy upon contact the microorganisms responsible for citrus plant disease; more specifically, to the diseases canker and greening.

In one aspect the invention relates to a synthetic lytic peptide wherein said lytic peptide exists in a beta configuration and is free of disulfide linkages said lytic peptide comprising about 40 or fewer amino acids.

In particular, the invention relates to lytic peptides having the peptide sequence:
FKLRAKVKIRLRAKIKL (SEQ ID: 1), FKIKARLRVKIKARLKL (SEQ ID: 2), FRIRAKVKLRIRAKVRL (SEQ ID: 3) or FRVKARIRLKVKARIRL (SEQ ID: 4).

In another embodiment, the invention provides an antimicrobial composition for treating diseases of citrus plants comprising a synthetic peptide having the following peptide sequence: FKLRAKVKIRLRAKIKL (SEQ ID: 1), FKIKARLRVKIKARLKL (SEQ ID: 2), FRIRAKVKLRIRAKVRL (SEQ ID: 3) or FRVKARIRLKVKARIRL (SEQ ID: 4) and combinations thereof.

In another aspect of the present invention, there is provided a synthetic lytic peptide wherein said lytic peptide exists in a beta configuration and possesses a cysteine disulfide linkage said lytic peptide comprising about 50 amino acids.

In particular, the synthetic lytic peptide has the following peptide sequence: KARLKFCKGLCIKIKVR (SEQ ID: 5), KIKARLCLGKFCIKARLK (SEQ ID: 6), KAFKKAFKKACFKGLCAKKFKKFAKKFAK (SEQ ID: 7) or KFAKKFKKFAKKFCFKGLCAFKKAFKKFKKAF (SEQ ID: 8).

In another embodiment, the invention provides an antimicrobial composition for treating diseases of citrus plants comprising a synthetic peptide having the following peptide sequence: KARLKFCKGLCIKIKVR (SEQ ID: 5), KIKARLCLGKFCIKARLK (SEQ ID: 6), KAFKKAFKKACFKGLCAKKFKKFAKKFAK (SEQ ID: 7) or KFAKKFKKFAKKFCFKGLCAFKKAFKKFKKAF (SEQ ID: 8) or combinations thereof.

In one aspect the invention relates to a synthetic lytic peptide wherein said lytic peptide exists in an alpha configuration and is free of disulfide linkages said lytic peptide comprising about 40 amino acids. In particular, the invention relates to a lytic peptide having the peptide sequence: FAFAFKAFKKAFKKFKKAFKKA.

In particular, the peptide compositions of the present invention are effective against the specific diseases canker and greening found in citrus plants.

In another embodiment, the novel peptides of the present invention are combined with a solvent, wherein a preferred solvent is water.

In yet another embodiment, the present invention provides a method of treating citrus canker or citrus greening comprising administering an effective amount of a synthetic lytic peptide having the peptide sequence: FKLRAKVKIRLRAK- IKL, FKIKARLRVKIKARLKL, FRIRAKVKLR-IRAKVRL, FRVKARIRLKVKARIRL, KARLKFCK-GLCIKIKVR, KIKARLCLGKFCIKARLK, KAFKKAFKKACFKGLCAKKFKKFAKKFAK, KFAKKFKKFAKKFCFKGLCAFKKAFKKFKKA or FAFAFKAFKKAFKKFKKAFKKA or combinations thereof.

Lytic peptides are small proteins that are major components of the antimicrobial defense systems of numerous species (AMPs). They are a ubiquitous feature of nearly all multi-cellular and some single-cellular life forms as described in Cary J W, Rajaselaran K, Jaynes J M, Cleveland T E 2005. Transgenic expression of a gene encoding a synthetic antimicrobial peptide results inhibition of fungal growth in vitro and in planta, Plant Sci, 154, 171-81. They generally consist of between 10-50 amino acids in length, which have the potential for forming discrete secondary structures. Often, they exhibit the property of amphipathy. An amphipathic α-helix may be depicted as a cylinder with one curved hemi-cylinder face composed primarily of non-polar amino acids while the other face is composed of polar amino acids.

Many of the lytic peptides with capacity to form an α-helix, which have been described in the literature (e.g. Jaynes J M 1989. Lytic peptides: harbingers of a new age in the treatment of disease. New Sci 42-44), seem to fall into one of three different classes (below) based, in part, on the arrangement of amphipathy and high positive charge density within the molecule.

1) Melittin (26 amino acids in length and derived from the Honeybee), C-terminal half amphipathic with the N-terminal half primarily hydrophobic. This peptide's primary role, as a component of bee venom, is protective in the sense of helping to provide part of the "toxicity" in a bee sting.
2) Cecropins (35 amino acids in length and derived from the Giant Silk Moth), N-terminal half amphipathic while the C-terminal half mostly hydrophobic as described in Bowman, H G, Kockum K, Lee J, Xanthapoulous, K G, Bennich H, Engstrom A, Merrifield B, Andreu D. 1985. On the primary structure of lysozyme, cecropins and attacins from Hyalophora cecropia, Dev Com Imm 9, 551-58. These types of peptides were shown to be induced upon bacterial infection of the insect and are a part of their non-humoral anti-prokaryotic immune system.
3) Magainins (23 amino acids in length and derived from the African Clawed Frog), amphipathic the full-length of the molecule as disclosed in Zasloff M, 1987 Magainins, a Class of Antimicrobial Peptides from Xenupus skin: isolation, characterization of two active forms and partial cDNA sequence of a precursor, Proc. Natl Acad Sci USA 84, 5449-53. This peptide is produced in the slimy secretion found on the skin of the amphibian and is primarily a protective compound against infection by prokaryotes.

Conservation of these physical properties is requisite for activity, but the requirements seem to be somewhat nonspecific in terms of amino acid sequence. All classes of lytic peptides differ somewhat in activity (note that Class 3, magainin class, is usually less active in cell membrane disruption than are the other lytic peptide classes) A number of highly sequence divergent analogs have been synthesized for each of the peptide classes and some have been found to be substantially more active and less toxic than their natural counterparts as reported in Rajasekaran, K, Jaynes, J M, and Cary, J W , Transgenic Expression of Lytic peptides In Food and Feed Crops to Control Phytopathogens and Preharvest Mycotoxin Contamination (2009) in Mycotoxin Prevention and Control in Agriculture, Chapter 9, 119-142. American Chemical Society Symposium Series Vol. 1031.

Citrus canker is a disease affecting citrus species. It is caused by the bacterium *Xanthomonas axonopodis*. Infection causes lesions on the leaves, stems, and fruit of citrus trees, including line, oranges and grapefruit. While not harmful to humans, canker significantly affects the vitality of citrus trees, causing leaves and fruit to drop prematurely; our fruit infected with canker is safe to eat, but too unsightly to be so.

The disease, which is believed to have originated in Southeast Asia, is extremely persistent. When it becomes established in an area. Citrus groves have been destroyed in attempts to eradicate the disease, Australia, Brazil and the United States are currently suffering from canker outbreaks.

Citrus greening disease is probably the worst disease of citrus caused by a bacteria pathogen. The causative agents are motile bacteria *Candidatus Liberibacter*. Transmission is by the Asian citrus psyllid (Sternorrhyncha: Psyllidae; the African citrus, psyllid, also known as the 2-spotted citrus psyllid. The disease was first described in 1929 and first reported in China in 1943. The African variation was first reported in 1947 in South Africa, where it is still widespread.

MIC for the purpose of this invention is the lowest concentration of an antimicrobial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents. An MIC is generally regarded as the most basic laboratory measurement of the activity of an antimicrobial agent against an organism. MBC is defined as the lowest concentration of an antimicrobial agent needed to kill 99.9% of the initial organism inoculum. Presently, specific guidelines for interpretation are not available; therefore, a clinician knowledgeable in both bactericidal testing and infectious diseases should be available to interpret the results.

Hemolysis as defined herein is an in vitro assay where the compounds tendency to lyse red blood cells is determined. Presumably, the compounds that are less hemolytic will be less toxic in vivo. Increasing amounts of compound are added to solutions containing red blood cells and left for a specified time and then lysis is determined spectrophotometrically by measuring hemoglobin release.

The numerical difference between the value of the mean of hemolysis and the mean of the activity, is a useful way to determine those peptides having the desired activity. Thus the lowest hemolytic behavior, especially those values close to zero, relate to the best killing.

Peptide Design

While not wishing to be bound by theory, the present inventor provides herein below a discussion of the physical and chemical aspects of protein and peptides which may relate to their function as antimicrobial agents.

Amphipathy, Hydrophobicity, & Charge Density: Physical Properties that Unify Protein Structure and Function To best illustrate the physical connections between proteins and peptides (including our own), it is necessary to display their sequences in ways that make it easier to visualize structural differences and similarities. If we view our peptides specifically, there are a number of physical features that appear to be important in modulating their activity:
1. Degree of amphipathy
2. Length of amphipathy
3. Heterogeneity of amphipathic section
4. Placement of amphipathic section (N or C terminal)
5. "+" Charge density (less or more)
6. Hydrophobicity of amphipathic section 7. Presence of hydrophobic tail
8. Length of hydrophobic tail
9. Hydrophobicity of tail
10. Placement of hydrophobic tail (N or C terminal)
11. Absence, presence, & position of "+" charged center
12. Absence or presence & position of flanking sequence
13. Predominating secondary structure
14. Termini modification (N-acetylation, C-amidation)
15. Surface area of hydrophilic and hydrophobic faces
16. Steric or volume considerations.

Some of the above properties may also account for the biological activity of other proteins and can also be causative factors of disease processes. These characteristics can be distinguished by viewing the amino acids in ways that visually accentuate the differences in their physical attributes. In this respect, it is instructive to ponder the evolution of protein structure and the fact that, generally speaking, only 20 different amino acids are found in proteins. These are: alanine (A), arginine (R), aspargine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tyrosine (Y), valine (V), and tryptophan (W). There are a few exceptions, but these 20 are the only ones that are represented in the genetic code (and are called the protein amino acids).

Taking these special 20 amino acids and viewing just two of their seemingly simple properties: hydrophobicity and volume differences can give one an appreciation of the significant chemical refinements that they must represent. The structural clues they provide in determining protein functionality are available, if we just look at them in the right way. For at least the last 2 billion years, life has found 20 amino acids, combined in different ways, to be adequate to meet all the challenges that it has faced on this planet. All the protein questions that will ever be asked can be answered by natural selection; and life, since the dawn of "biological" time, has been "compelled" to solve just a miniscule number of structural problems. There may be around a trillion different proteins that have ever existed on the earth. By applying combinatorial mathematics to the 20 amino acids, results in practical terms, an almost infinite number of possible combinations that becomes an even bigger number as the length of the protein is increased. For example, if the maximum length for a protein is 200 amino acids, then, the total number of different proteins possible can be derived from the formula found below (see sum of a finite geometric series below):

$$\sum_{i=2}^{200} 20^i = a^1 \frac{1-r^n}{1-r}$$

"$a^1$" is the first term, "n" is the number of terms, and "r" is the common ratio of the series increase, i.e., it goes up by a factor of 20 each time (the number of different protein amino acids). When one goes through the arithmetic, the number of possible combinations of proteins, from two amino acids in length to 200, is $8.458 \times 10^{257}$. A huge number to say the least, particularly, when one considers that the total number of atoms of matter in the universe is estimated to be less than $10^{100}$! Also, it should be noted that there are many proteins far larger than 200 amino acids in length. The point of this exercise is that life, in 2 billion years of existence, has not significantly diminished the total number of possible assembled amino acid combinations (proteins) that can do all of the different jobs required by all living organisms. That is the power of evolution; biology will derive suitable answers to any question, given enough time. By studying the predominating 20 protein amino acids in certain ways, we can gain insight into the structural principles that govern all of protein biochemistry and then, as our awareness increases, subtle connections are discovered and seeming disparities can be replaced by recognizable physical commonalties. The unity of the protein structure/function paradigm will continue to emerge as our understanding deepens. After all, every protein that ever existed has been tempered in the "forge" of natural selection. The recognizable similarities of protein structure, even taken from widely divergent species, should not come as a surprise—all of life's processes will ultimately be shown to be interconnected throughout their numerous levels of complexity.

Lytic Peptide Design Parameters

Lytic peptides (sometimes called Peptidyl Membrane Interactive Peptides [MIM's] are small basic proteins that appear to be major components of the antimicrobial defense systems of a number of animal species including insects, amphibians, and mammals. They consist of 23-39 amino acid peptides, which have potential for forming amphipathic α-helices or partial β-pleated sheets (locked by disulfide linkages); and thus, can interact with all cell types at the membrane surface. This interaction can result in, either no observable cellular effect, temporary cell impairment, death, or cell proliferation. That is why these molecules are more than lytic peptides. Four distinct types of peptides were discovered in the last decade; examples of each type are melittin, cecropins, magainins and defensins. The properties of naturally occurring peptides suggest at least three distinct α-helical classes consisting of different arrangements of amphipathic and hydrophobic regions:

Synthetic Lytic Peptides

A. The synthetic lytic peptides in a beta configuration free of disulfide linkage of the present invention (AGM 155, 176, 178 and 179) provide a completely novel class of synthetic peptides that form β-sheets without the necessity of disulfide linkages. The only natural lytic peptides that assume a β-conformation are the defensins and defensin-like molecules. They can assume this shape because of intra-disulfide linkages that lock them into this form, an absolute requisite for activity. In a case of D4E1 those skilled in the art assume a beta sheet forms naturally because of alternating hydrophobic and charged hydrophilic amino acids.

B. The synthetic lytic peptides having a beta configuration and a cysteine disulfide link (AGM181-184) of the present invention arise from the opportunity to improve upon the safety and efficacy of certain natural, similarly structured peptides PR-39 and Tachyplesin (TP). The former is an antimicrobial peptide found in swine and the latter is a defensin-like peptide found in the hemolymph of the horseshoe crab. Both represent components of the innate immune system that is ubiquitous across higher life. There are perceived regulatory issues with the use of "natural" peptides and proteins so it is of interest to design totally synthetic ones for GM work.

The amino acid sequences for both natural and synthetic peptides are shown below.

PR39

RRRPRPPYLPRPRPPPFFPPRLPPRIPPGFPPRFPPRFP

Tachyplesin

KWCFRVCYRGICYRRCR

PR39 is known to possess activities in mammals including stimulation of angiogenesis that could be a problem for any human coming in contact with it. TP is a defensin type peptide. It has been demonstrated that defensins are not really suitable to develop as drugs for human use. They are inactivated by blood-components and often possess diminished and less broad activities and in extensive tests my designed molecules have superior properties over defensins for use as human drugs. The animal origin of TP is reason enough to abandon it.

A comparison of antimicrobial activity for these two naturally occurring peptides against various pathogens (combined fungal and bacterial) is summarized below

| Pathogen | TP MIC$_{80}$ | D4E1 MBC$_{100}$ |
|---|---|---|
| *Aspergillus flavus* | 34 | 12 |
| *Aspergillus fumigatus* | ND | 12 |
| *Fusarium moniliforme* | 21 | 3 |
| *Fusarium oxysporum* | ND | 3 |
| *Erwinia stewartii* | ND | 1 |
| *Xanthomonas campestris* | 0.77 | 2 |

*Note
that the numbers are µM concentration necessary to achieve the level of control indicated.
MIC$_{80}$ is the concentration of TP necessary to limit growth by 80%.
The MBC$_{100}$ is the concentration of D4E1 necessary to kill 100% of the pathogens tested.

DETAILED DESCRIPTION OF THE INVENTION

Synthesis of Lytic Peptides

Lytic peptides were synthesized by Polypeptide Laboratories (San Diego, Calif.) utilizing solid-phase F-Moc chemistry.

After extraction and column chromatography, the purity of the peptides was determined by high performance liquid chromatography (HPLC). HPLC profiles of the synthesized peptides indicated a purity of more than 95%.

A listing of the amino acid sequences of these peptides is found in Table I below

TABLE I

| Name | Sequence | # AA | MWT* |
|---|---|---|---|
| AGM 155 | FKLRAKVKIRLRAKIKL | 17 | 2635.72 |
| AGM 176 | FKIKARLRVKIKARLKL | 17 | 2635.72 |
| AGM 178 | FRIRAKVKLRIRAKVRL | 17 | 2677.73 |
| AGM 179 | FRVKARIRLKVKARIRL | 17 | 2677.73 |
| AGM 181 | KARLKFCFKGLCIKIKVR | 18 | 3646.82 |
| AGM 182 | KIKARLCLGKFCIKARLK | 18 | 2584.74 |
| AGM 183 | KAFKKAFKKFKKACFKGLCAKKFKKFAKKFAK | 32 | 4740.86 |
| AGM 184 | KFAKKFKKFAKKFCFKGLCAFKKAFKKFKKAF | 32 | 4776.96 |
| D4E1 | FKLRAKIKVRLRAKIKL | 17 | 2365.72 |

Determination of the Antibacterial Activity of the Peptides

Minimum Inhibitory Concentration or MIC for the purpose of this invention is the lowest concentration of an antimicrobial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents. A MIC is generally regarded as the most basic laboratory measurement of the activity of an antimicrobial agent against an organism. MBC is defined as the lowest concentration of an antimicrobial agent needed to kill 99.9% of the initial organism inoculum. Presently, specific guidelines for interpretation are not available; therefore, a clinician knowledgeable in both bactericidal testing and infectious diseases should be available to interpret the results.

MICs were determined by the broth microdilution method described by the National Committee for Clinical Laboratory Standards (17). Serial twofold dilutions of each peptide solution were prepared (final volume, 100 ml) in microtiter trays with appropriate medium. Each dilution series included control wells containing bacteria without peptide. A total of 100 ml of the adjusted inoculum (100,000 organisms) was added to each well, and then the trays were incubated at in ambient air overnight (18 to 24 h). The MIC of each peptide for each isolate was read as the lowest concentration of peptide that inhibited visible growth of the organism.

Determination of Hemolytic Activity of the Peptides

Hemolysis as defined herein is an in vitro assay where the compounds tendency to lyse red blood cells is determined. Presumably, the compounds that are less hemolytic will be less toxic in vivo. Increasing amounts of compound are added to solutions containing red blood cells and left for a specified time and then lysis is determined spectrophotometrically by measuring hemoglobin release.

A small volume of a suspension of erythrocytes (about 100 million) is kept on ice with a specific amount of lytic peptide. The cells are then placed in a 37° C. water bath for 10 min, vortexed and centrifuged at 1000 g for 2 min. The supernatant was removed and the amount of hemoglobin that was released was determined by the samples' absorbance at 412 nm. Control values without added peptide were subtracted from the absorbance readings.

Use of Mean Difference

The numerical difference between the value of the mean of hemolysis and the mean of the activity is a useful way to determine those peptides having the most desired activity. Thus the mean differences closest to zero possess the optimal activities, i.e. high level of killing while retaining low level of hemolysis.

The above in vitro tests and analyses were conducted on a set of designed peptides of the present invention; and, for comparative purposes, naturally derived molecules. The results of these tests are displayed in Table II and Table III below. The mean difference values for the peptides of the present invention clearly demonstrate new and superior levels of activity.

In Table I, AGM 155, 176, 178 and 179 are Examples of lytic peptides of the present invention having a beta configuration and are free of disulfide linkages. In Table II, AGM 181-184 are examples of the present invention of lytic peptides having beta configuration and possessing a cysteine disulfide linkage

TABLE II

| Peptide | Mean Activity in µM | Mean of Hemolysis in µM | Mean Difference |
|---|---|---|---|
| AGM 155 | 0.7 | 1.6 | −1.13 |
| AGM 176 | 1 | 1.3 | −0.61 |
| AGM 178 | 1 | 1.2 | −0.4 |

TABLE II-continued

| Peptide | Mean Activity in μM | Mean of Hemolysis in μM | Mean Difference |
| --- | --- | --- | --- |
| AGM 179 | 3 | 2.1 | 0.44 |
| Apidaecin IA | 20.67 | 1.6 | 19.06 |
| Drosocin | 21 | 1.6 | 19.31 |
| Histatin-5 | 30 | 1.8 | 28.25 |
| Indolicidin | 5.33 | 2 | 3.41 |
| LL-37 | 1 | 5.1 | −4.29 |
| Pyrrhocoricin (D) | 23.33 | 1.9 | 21.63 |
| SMAP-29 | 0.53 | 3.2 | −2.65 |
| Tachyplesin I | 0.3 | 3 | −2.88 |
| D2A21 | 0.77 | 8.4 | −8.38 |
| D4E1 | 0.77 | 3.6 | −2.76 |
| Pyrrhocoricin (H) | 26.67 | 1.6 | 24.94 |
| α-Purothionin | 12.05 | 22.5 | −11.37 |
| Cecropin A | 3.83 | 1.1 | 2.29 |
| Cecropin B | 6.17 | 1.2 | 4.51 |
| Magainin I | 30 | 1.3 | 28.41 |
| Magainin II | 30 | 1.5 | 28.47 |
| Melittin | 1.33 | 100.8 | −96.59 |

TABLE III

| Peptide | MIC for B1 | MIC for B2 | MIC for B3 | Mean |
| --- | --- | --- | --- | --- |
| AGM 181 | 1 | 0.3 | 1 | 0.77 |
| AGM 182 | 1 | 0.3 | 1 | 0.77 |
| AGM 183 | 3 | 0.3 | 1 | 1.44 |
| AGM 184 | 1 | 0.3 | 1 | 0.77 |

B1 = *agrobacterium*
B2 = *Sinorhizobium*
B3 = *Xanthomonas*

BRIEF DESCRIPTION OF DRAWINGS:

FIG. 1

Figure 2:
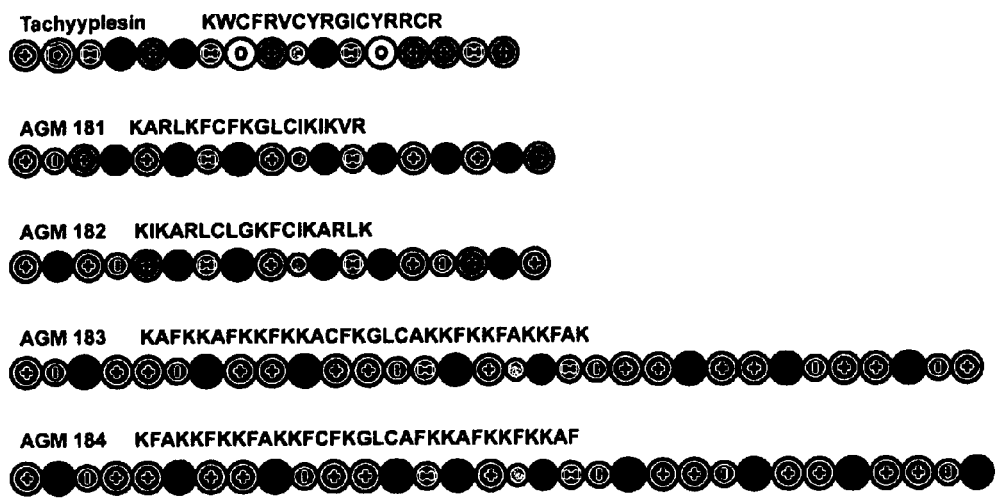
Figure 2:
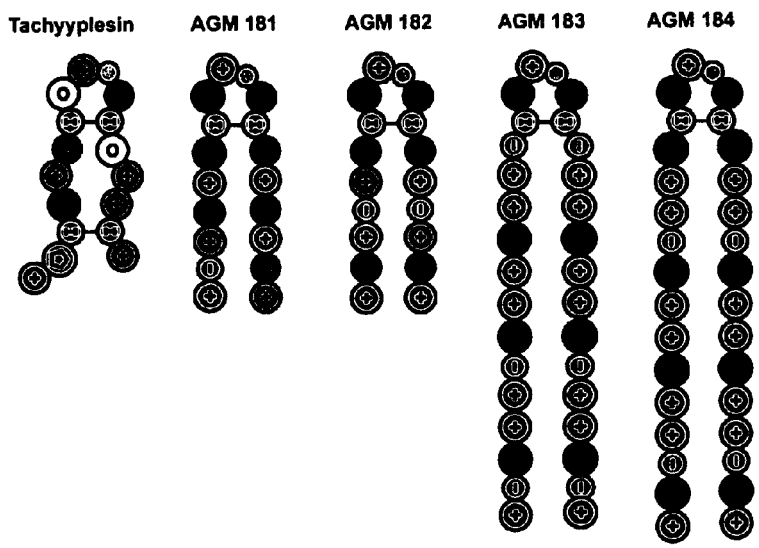

Four distinct types of peptides were discovered in the last decade; two examples of each type are shown melittin, cecropins, magainins and defensins. The properties of naturally occurring peptides suggest at least three distinct a-helical classes consisting of different arrangements of amphipathic and hydrophobic regions.

FIG. 2

The arrangement of amphipathic and hydrophobic regions of the newly designed peptides are found above. AGM 181 is SEQ ID: 5. AGM 182 is SEQ ID: 6. AGM 183 is SEQ ID: 7. AGM 184 is SEQ ID: 8.

The invention claimed is:

1. A synthetic lytic peptide wherein said lytic peptide exists in a beta configuration and is free of disulfide linkages and comprises a peptide sequence selected from the group consisting of FKLRAKVKIRLRAKIKL (SEQ ID: 1), FKIKARLRVKIKARLKL (SEQ ID: 2), and FRIRAKVKLRIRAKVRL (SEQ ID: 3).

2. An antimicrobial composition for treating citrus canker disease and citrus greening disease comprising an effective amount of a peptide according to claim 1 comprising a peptide sequence selected from the group consisting of FKIKARLRVKIKARLKL (SEQ ID: 2), and FRIRAKVKLRIRAKVRL(SEQ ID NO:3).

3. The composition for treating diseases according to claim 2 further comprising a solvent.

4. The composition according to claim 3 wherein said solvent is water.

* * * * *

SEQUENCE LISTING

```
<160> NUMBER OF SEQ ID NOS: 24

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 1 ttt aaa ctt cgt gct aaa gtt aaa att cgt ctt cgt gct aaa att aaa      48
Phe Lys Leu Arg Ala Lys Val Lys Ile Arg Leu Arg Ala Lys Ile Lys
1               5                   10                  15 ctt                                                                   51
Leu

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 2 ttt aaa att aaa gct cgt ctt cgt gtt aaa att aaa gct cgt ctt aaa      48
Phe Lys Ile Lys Ala Arg Leu Arg Val Lys Ile Lys Ala Arg Leu Lys
1               5                   10                  15 ctt                                                                   51
Leu

<210> SEQ ID NO 3
<211> LENGTH: 51
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 3 ttt cgt att cgt gct aaa gtt aaa ctt cgt att cgt gct aaa gtt cgt    48
Phe Arg Ile Arg Ala Lys Val Lys Leu Arg Ile Arg Ala Lys Val Arg
1               5                   10                  15 ctt                                                                51
Leu

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 4 ttt cgt gtt aaa gct cgt att cgt ctt aaa gtt aaa gct cgt att cgt    48
Phe Arg Val Lys Ala Arg Ile Arg Leu Lys Val Lys Ala Arg Ile Arg
1               5                   10                  15 ctt                                                                51
Leu

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 5 ttt aaa ctt cgt gct aaa gtt aaa att cgt ctt cgt gct aaa att aaa    48
Phe Lys Leu Arg Ala Lys Val Lys Ile Arg Leu Arg Ala Lys Ile Lys
1               5                   10                  15 ctt                                                                51
Leu

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 6 ttt aaa att aaa gct cgt ctt cgt gtt aaa att aaa gct cgt ctt aaa    48
Phe Lys Ile Lys Ala Arg Leu Arg Val Lys Ile Lys Ala Arg Leu Lys
1               5                   10                  15 ctt                                                                51
Leu
```

```
<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(48)

<400> SEQUENCE: 7 ttt cgt att cgt gct aaa gtt aaa ctt cgt att cgt gct aaa gtt cgt      48
Phe Arg Ile Arg Ala Lys Val Lys Leu Arg Ile Arg Ala Lys Val Arg
1               5                   10                  15

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 8 ttt cgt gtt aaa gct cgt att cgt ctt aaa gtt aaa gct cgt att cgt      48
Phe Arg Val Lys Ala Arg Ile Arg Leu Lys Val Lys Ala Arg Ile Arg
1               5                   10                  15 ctt                                                                  51
Leu

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 9 aaa gct cgt ctt aaa ttt tgt aaa ggt ctt tgt att aaa att aaa gtt      48
Lys Ala Arg Leu Lys Phe Cys Lys Gly Leu Cys Ile Lys Ile Lys Val
1               5                   10                  15 cgt                                                                  51
Arg

<210> SEQ ID NO 10
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(87)

<400> SEQUENCE: 10 aaa att aaa gct cgt ctt tgt ctt ggt aaa ttt tgt att aaa gct cgt      48
Lys Ile Lys Ala Arg Leu Cys Leu Gly Lys Phe Cys Ile Lys Ala Arg
1               5                   10                  15
```

```
ctt aaa aaa ttt aaa aaa ttt gct aaa aaa ttt gct aaa        87
Leu Lys Lys Phe Lys Lys Phe Ala Lys Lys Phe Ala Lys
            20                  25
```

<210> SEQ ID NO 11
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(96)

<400> SEQUENCE: 11

```
aaa ttt gct aaa aaa ttt aaa aaa ttt gct aaa aaa ttt tgt ttt aaa        48
Lys Phe Ala Lys Lys Phe Lys Lys Phe Ala Lys Lys Phe Cys Phe Lys
1               5                   10                  15 ggt ctt tgt gct ttt aaa aaa gct ttt aaa aaa ttt aaa aaa gct ttt        96
Gly Leu Cys Ala Phe Lys Lys Ala Phe Lys Lys Phe Lys Lys Ala Phe
            20                  25                  30
```

<210> SEQ ID NO 12
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(66)

<400> SEQUENCE: 12

```
ttt gct ttt gct ttt aaa gct ttt aaa aaa gct ttt aaa aaa ttt aaa        48
Phe Ala Phe Ala Phe Lys Ala Phe Lys Lys Ala Phe Lys Lys Phe Lys
1               5                   10                  15 aaa gct ttt aaa aaa gct                                                66
Lys Ala Phe Lys Lys Ala
            20
```

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Phe Lys Leu Arg Ala Lys Val Lys Ile Arg Leu Arg Ala Lys Ile Lys
1               5                   10                  15

Leu
```

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Phe Lys Ile Lys Ala Arg Leu Arg Val Lys Ile Lys Ala Arg Leu Lys
1               5                   10                  15

Leu
```

```
<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Arg Ile Arg Ala Lys Val Lys Leu Arg Ile Arg Ala Lys Val Arg
1               5                   10                  15

Leu

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Arg Val Lys Ala Arg Ile Arg Leu Lys Val Lys Ala Arg Ile Arg
1               5                   10                  15

Leu

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Lys Leu Arg Ala Lys Val Lys Ile Arg Leu Arg Ala Lys Ile Lys
1               5                   10                  15

Leu

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Lys Ile Lys Ala Arg Leu Arg Val Lys Ile Lys Ala Arg Leu Lys
1               5                   10                  15

Leu

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Arg Ile Arg Ala Lys Val Lys Leu Arg Ile Arg Ala Lys Val Arg
1               5                   10                  15
```

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Arg Val Lys Ala Arg Ile Arg Leu Lys Val Lys Ala Arg Ile Arg
1               5                   10                  15

Leu

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Ala Arg Leu Lys Phe Cys Lys Gly Leu Cys Ile Lys Ile Lys Val
1               5                   10                  15

Arg

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ile Lys Ala Arg Leu Cys Leu Gly Lys Phe Cys Ile Lys Ala Arg
1               5                   10                  15

Leu Lys Lys Phe Lys Lys Phe Ala Lys Lys Phe Ala Lys
                20                  25

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Phe Ala Lys Lys Phe Lys Lys Phe Ala Lys Lys Phe Cys Phe Lys
1               5                   10                  15

Gly Leu Cys Ala Phe Lys Lys Ala Phe Lys Lys Phe Lys Lys Ala Phe
                20                  25                  30

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 24

Phe Ala Phe Ala Phe Lys Ala Phe Lys Lys Ala Phe Lys Lys Phe Lys
1               5                   10                  15

Lys Ala Phe Lys Lys Ala
            20
```